United States Patent

Gluck

[11] Patent Number: 5,147,307
[45] Date of Patent: Sep. 15, 1992

[54] ANATOMICAL MARKER DEVICE AND METHOD

[76] Inventor: Seymour M. Gluck, 1204 Beach 9th St., Far Rockaway, N.Y. 11691

[21] Appl. No.: 716,823

[22] Filed: Jun. 17, 1991

[51] Int. Cl.$^5$ .................................. A61M 5/00
[52] U.S. Cl. ........................ 604/116; 604/157
[58] Field of Search ........... 604/115, 116, 192, 157; 128/DIG. 6; 606/202

[56] References Cited

U.S. PATENT DOCUMENTS

| | | | |
|---|---|---|---|
| 1,561,116 | 11/1925 | Silliman | 604/115 |
| 1,824,516 | 9/1931 | Tyvand | 604/115 |
| 1,991,103 | 2/1935 | King | 604/157 |
| 2,103,174 | 12/1937 | Posada | 604/115 |
| 2,234,961 | 3/1941 | Canada | 604/115 |
| 2,730,099 | 1/1956 | Sullivan | 604/157 |
| 3,324,854 | 6/1967 | Weese . | |
| 3,542,022 | 11/1970 | Bartnik . | |
| 4,196,735 | 4/1980 | Ayer | 604/115 |
| 4,314,568 | 2/1982 | Loving . | |
| 4,576,185 | 3/1986 | Proud et al. | 604/192 |
| 4,580,561 | 4/1986 | Williamson . | |
| 4,586,924 | 5/1986 | Lanning | 604/115 |
| 4,636,201 | 1/1987 | Ambrose et al. | 604/192 |
| 4,667,679 | 5/1987 | Sahota . | |
| 4,767,412 | 8/1988 | Hymanson | 604/192 |
| 4,816,024 | 3/1989 | Sitar et al. | 604/192 |

*Primary Examiner*—Paul J. Hirsch
*Attorney, Agent, or Firm*—Bryan Cave

[57] ABSTRACT

A device and method for locally and directionally marking the surface of the skin where a diagnostic or therapeutic procedure is to be performed utilizing a hand-held marking device comprising a supporting body having one or more thin-edged, tapered patterning elements extending in relief therefrom. The patterning elements are impressed into the skin to produce temporary directional and positioning markings capable of delineating a selected target site. The area is then rendered antiseptic and the desired procedure is carried out using the directional and positional guidance afforded by the markings.

20 Claims, 4 Drawing Sheets

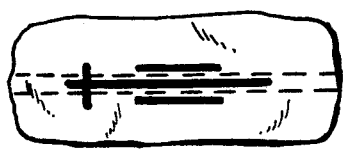
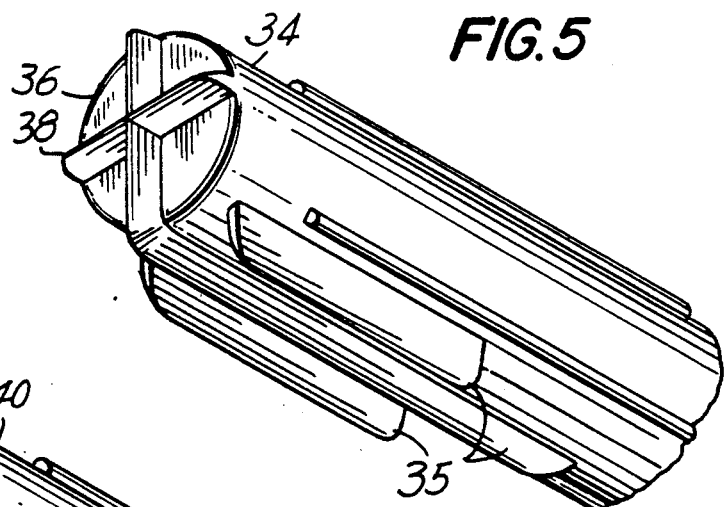
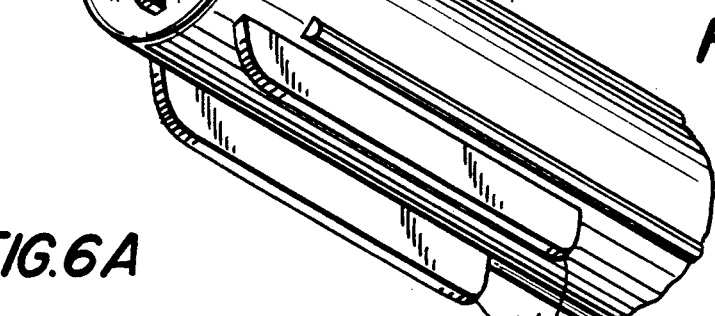
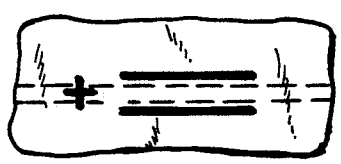
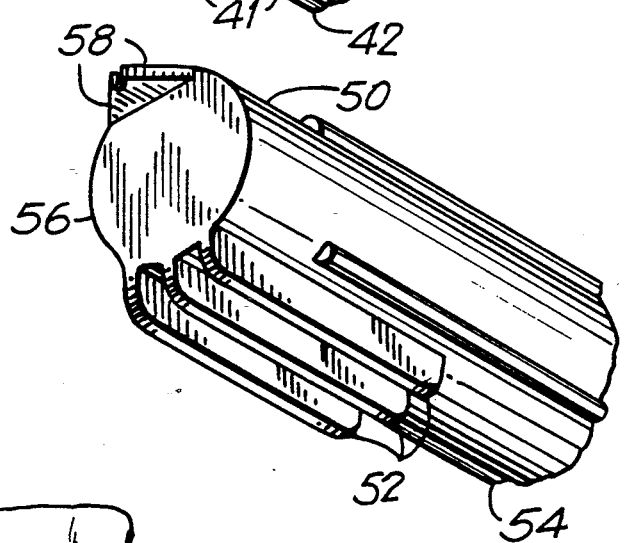
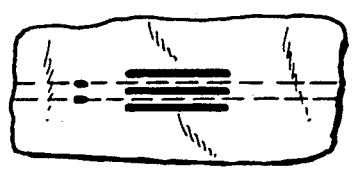

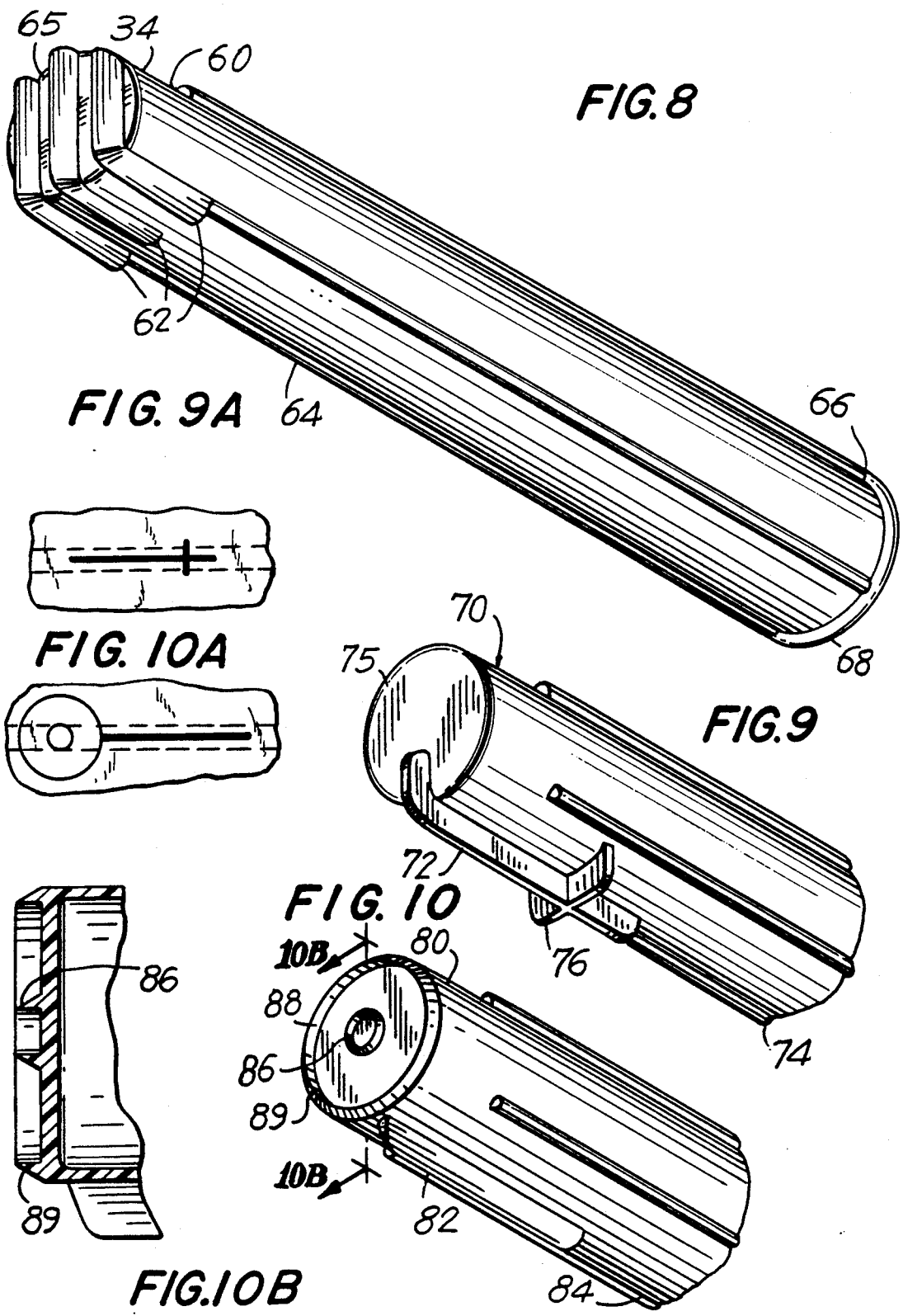

ANATOMICAL MARKER DEVICE AND METHOD

This invention relates to a hand-held marker device which delineates a site on the skin where a therapeutic and/or diagnostic procedure is to be performed and method of using said marker.

BACKGROUND OF THE INVENTION

When invasive diagnostic or therapeutic procedures are to be performed which penetrate the skin, the health worker must accurately define the targeted area and designate a preferred point of entry. This is usually accomplished by a combination of visual inspection and palpation, followed by appropriate antiseptic procedures.

Various specialized devices are employed to enter subcutaneous tissues, blood vessels, muscles and other structures accessible through the skin, to obtain blood samples and biopsy specimens, or for the administration of medications, nutrients, blood transfusions and intravenous fluids. Such devices and their commonly associated components may include hypodermic needles, syringes, cannulas, vacuum tubes, catheters, probes, scalpels, biopsy punches and the like, depending upon the required diagnostic or therapeutic applications desired.

A variety of anatomical areas may be selected, depending on the particular requirements. For example, the hands and arms are usually preferred areas for the retrieval of blood specimens or for the placement of intravenous lines to administer transfusions, fluids, medications and selected diagnostic agents.

Considerable care and precision are required to ensure accurate instrument placement within the constraints of strict antiseptic protocol. Selected sites are generally targeted and localized by means of visual inspection and direct palpation. Because spatial memory is notoriously transient and imprecise, recall is often reinforced by accessible landmarks such as skin creases, scars, blemishes and area of local pigmentation capable of providing convenient points of reference and supportive visual cues.

In the absence of reliable visual information, repetitive palpation is usually required for precise orientation. Once a target is selected, antimicrobial procedures are instituted to render the area antiseptically clean This is generally accomplished by washing and the application of germicidal agents such as alcohol and iodine. After an antiseptic barrier has been established, operators must depend on prior orientation and supportive visual cues to delineate a final approach to the targeted site. Repetitive palpation at this time runs the risk of contaminating the antiseptically prepared area and thus is to be avoided. However, since spatial orientation is usually transient and uncertain, particularly in the absence of guiding landmarks, repeated palpation is often attempted even though additional manipulation presents needless opportunities for the transfer and dissemination of pathogenic microorganisms.

Such breaches of antiseptic protocol can be crucial for hospitalized patients who are exposed to repeated blood tests, multiple injections, continuous intravenous infusions and similar invasive procedures by doctors, nurses and technicians working in a potentially infectious environment under less than ideal conditions.

Thus a hand-held device that conveniently and temporarily impresses distinctive markings into the surface of the skin capable of accurately defining a selected target and directionally guiding an operator to a designated site-of-entry, without endangering antiseptic safeguards, offers significant advantages in safety and precision over methods and means heretofore employed.

SUMMARY OF THE INVENTION

The marker of the invention is a simply constructed device which transiently impresses a mark on the skin to pinpoint a selected target prior to the establishment of an antiseptic field. By initially marking the targeted site and providing a visible frame of reference, any need to re-explore the targeted area following the establishment of an antiseptic field is virtually eliminated, and the potential for subsequently contaminating the site and infecting the patient is correspondingly reduced.

It should be understood that the marking device and method of the present invention is applicable to marking the skin of both humans and animals, in connection with any diagnostic or therapeutic procedure in which such marking may be helpful.

Markings are produced by one or more distinctive firm but not sharp elements extending in relief from the marker's supporting body. The patterning elements may project outwardly from the supporting body of the marker or be defined by an indentation in the body to define an intaglio-like construction; in either case, the patterning elements provide a relief pattern capable of being impressed into the skin surface to leave directional and positional markings thereon for several minutes. Use of the marker allows ample time for subsequent orientation, cleansing and antiseptic preparation of the targeted site prior to instrument placement.

Use of the marker of the invention is superior to marking the skin in other ways, for example, by use of an ink stamp. Use of the latter may result in inaccurate targeting of anatomical sites since tentative or improper initial placements may lead to false markings, smudges or the like. Moreover, ink markings may interfere with subsequent antiseptic steps or, indeed, be removed by alcohol or other antiseptic preparations.

The marker can be produced as either a free-standing, self-contained unit or its directional and positioning patterning elements can be advantageously incorporated into the construction or assemblage of diverse medical implements such as needle sheaths, syringes, probes, containers, protective wrappings, surgical trays, infusion sets and the allied paraphernalia commonly associated with diagnostic and/or therapeutic procedures. As used herein, the term "device" is intended to embrace any such unit or assemblage.

BRIEF DESCRIPTION OF THE DRAWINGS

FIG. 5 is a perspective view of a needle sheath, showing the patterning elements of a marker of the invention formed integrally therewith;

FIG. 5A is a top view of a mark made by the marker of FIG. 5;

FIGS. 6-7 are perspective views of alternate embodiments of needle sheaths having markers of the invention integral therewith;

FIGS. 6A and 7A are top views of marks made by the markers of FIGS. 6 and 7, respectively;

FIG. 8 is a perspective view of a needle sheath having marking elements along its longitudinal axis as well as at its open and closed ends;

FIG. 9 is a perspective view of an alternate needle sheath having a cross-shaped marker integral therewith;

FIG. 9A is a top view of the mark made by the marker of FIG. 9;

FIG. 10 is a perspective view of another needle sheath having a marker provided by a relief element projecting from a recessed, closed end cap; a second relief element defined by a tapered projection of the sheath wall beyond the surface of the recessed cap; and a third projection extending lengthwise from the supporting body of the sheath.

FIG. 10A is a top view of an impression made on the skin by the marker of FIG. 10;

FIG. 10B is a partial section through the needle sheath of FIG. 10, taken along line 10B-10B.

DETAILED DESCRIPTION OF THE INVENTION

The invention will be further described by reference to the Drawings.

Figure 1:
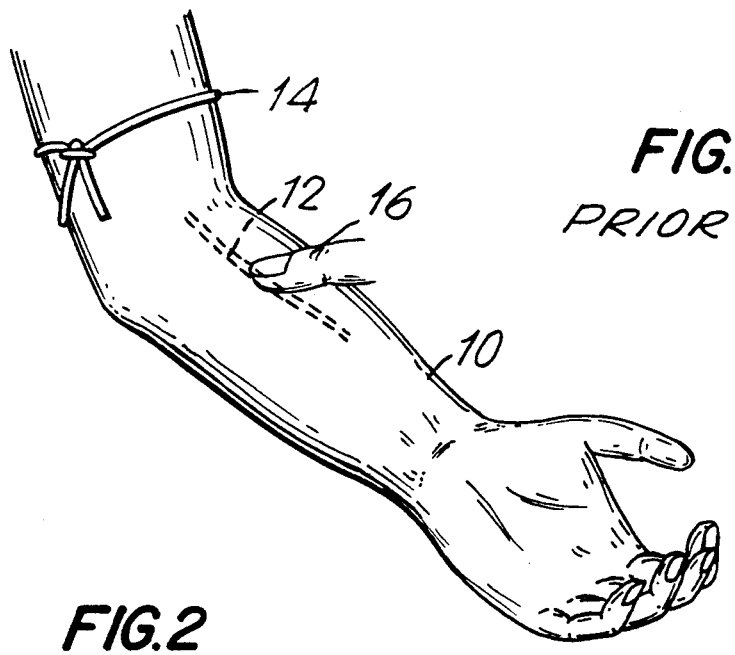
FIG. 1 is a planar view Of an arm illustrating a prior art method of locating an intravenous entry point.

FIG. 1 is a view of an arm illustrating a prior art method of targeting an intravenous entry point. An arm 10 having a vein 12 embedded therein and a tourniquet 14 applied to help locate the vein, is palpated at a likely location with a finger 16 of the operator. Thereafter the operator is obliged to remember where the vein is located if it cannot be readily visualized after completing the antiseptic preparation of the targeted site.

Figure 2:
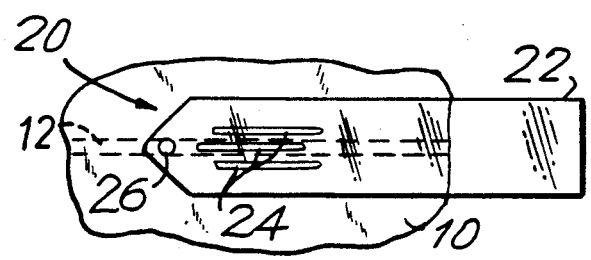
FIG. 2 is a top view of a marker of the invention.

FIG. 2 is a view of a marker 20 of the invention comprising a semi-rigid body 22, which can be of any convenient size and shape, having semi-rigid, tapered and thin-edged, linear patterning projections 24 extending therefrom and a thin-edged, tapered, circular vein-entry point marker 26.

Figure 2A:
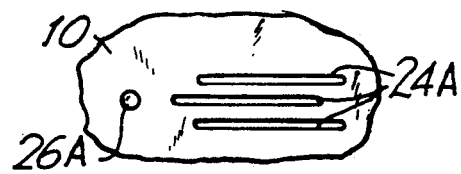
FIG. 2A is a top view of the mark made by the marker of FIG. 2.

FIG. 2A is a top view of the mark made by the marker 20 of FIG. 2 showing three parallel skin markings 24A and a circular mark 26A corresponding, respectively, to the projections 24 and 26. The center mark 24A is aligned with the circular mark 26A made by the vein-entry point marker 26.

The patterning projections project angularly outwardly from the body, substantially perpendicularly, to a height at least about 0.2 mm to about 2.0 mm, most preferably about 0.4-1.5 mm, above the adjacent surface of the supporting body. The patterning projections must be suitably tapered and sufficiently rigid to clearly and easily impress the skin. The overall size, projective height, and pattern of the patterning projections may vary with different embodiments and requirements for use of the marker of the invention.

The body and patterning projections of the markers of the invention can be made of any convenient material, such as plastic, metal, wood, hard rubber, glass or other composite material of the desired resiliency, i.e., to allow for temporarily impressing a mark on the skin.

The selection of a particular size embodiment is determined largely by the nature and location of the intended procedure. For example, to impress a mark on the hand or arm for an anticipated venipuncture, the patterning projections 24 must be fairly small to localize the area of placement. Larger patterning projections are more appropriate for marking sites intended for deep intramuscular injections, as, for example, the buttock area.

The patterning projections can be a single projection or multiple projections as shown in FIG. 2 and may encompass any convenient geometric configuration. When two projections are provided for positional and directional marking, e.g., for venipuncture, they may be spaced up to about 6 mm from one another. Alternatively, when as shown in the embodiment of FIG. 2, three projections are provided, they are preferably spaced about 2 to 3 mm from one another to both position entry point marker 26 on the vein and define the direction of entry by patterning projections 24. (Although, as in the embodiment of FIG. 2 multiple patterning projections complement one another by integrating and coordinating both positional and directional functions, it will be understood configuring elements of some embodiments of the marker of the invention may serve solely as positioning guides to locate a targeted site or to pinpoint a final point of entry.)

Figure 3:
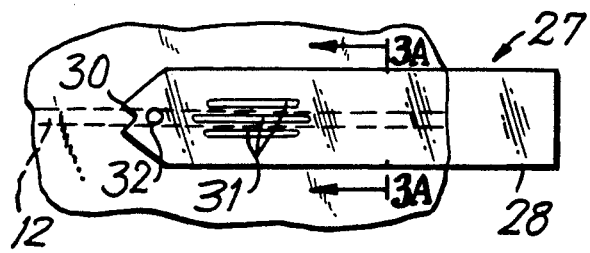
FIG. 3 is a top view of an alternate embodiment of the marker of the invention.
Figure 3A:
FIG. 3A is a cross sectional view of the marker of FIG. 3 taken along the line 3A—3A of FIG. 3.
Figure 3B:
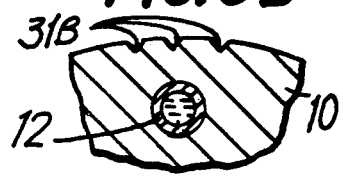
FIG. 3B is a cross sectional view of an arm marked in accordance with the invention.

FIG. 3 is a top view of an alternate marker 27 of the invention having a body 28 and a vee shaped end 30 which allows an operator to align and target a selected entry point. The linear projections 31 provide essentially directional guidance, orienting the operator toward the ultimate target. The circular projection 32 guides the operator toward a point of final entry into the vein. FIG. 3A is a cross sectional view of the body 28 of the marker 27 showing the linear projections 31 of FIG. 3. FIG. 3B is a corresponding partial cross sectional view of an arm 10 having a vein 12 therein, and illustrating the three temporary markings or indentations 31B made with the linear projections 31 shown in FIG. 3A.

The bodies 22 and 28 of FIGS. 2 and 3, respectively, are constructed of a conveniently thumb sized, transparent acrylic plastic with one or more directional and positioning patterning projections integrally molded thereon. Alternatively, the patterning projections may be composed of materials different from those of the bodies or possess other desirable characteristics such as a distinctive coloring. Such projections can be made separately and affixed to or inserted into the supporting body, as by means of glue, cement and the like.

The markers 20 and 27 of FIGS. 2 and 3 can be constructed from suitable plastics such as acrylics, polyethylene or polypropylene, which are preferred because they are readily produced, are inexpensive and are conveniently disposable. Other materials such as metal, wood, hard rubber and composites of the desired resiliency can be interchangeably employed.

It is to be understood that the patterning projections (e.g., 24, 26, 31 and 32) must be sufficiently thin-edged and tapered to impress a suitable pattern on the skin under slight to moderate pressure, but not so thin as to penetrate or injure the skin when properly employed.

Figure 4:
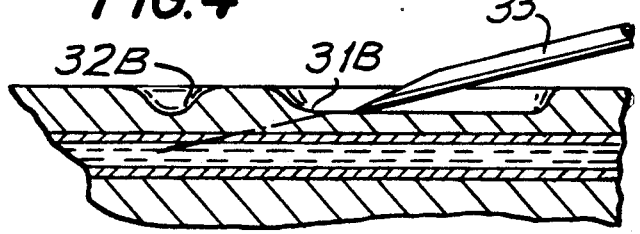
FIG. 4 is a longitudinal, cross sectional view of an arm illustrating a method of locating an intravenous entry point according to the invention
Figure 4A:
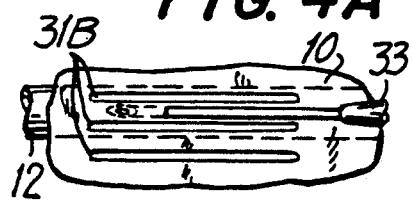
FIG. 4A is a top, expanded view of an alternate location of an intravenous entry point determined by a channel defined between two linear impressions formed by a marker of FIGS. 2 or 3.

FIG. 4 is a longitudinal cross sectional view of an arm 10 illustrating linear and circular impressions or marks 31B and 32B respectively, made by the marker 27 of FIG. 3 and illustrating an invasive device 33 being inserted into the arm 10 using the central linear mark 31B and the circular mark 32B as guides to the orientation of and desired entry into the vein 12. FIG. 4A shows an alternate placement of the invasive device 33 being inserted into the arm 10 using a channel between the marks 31B as a guide towards the vein 12. For purposes of venipuncture the directional orientation along a targeted vein may be axially guided by the linear projections 31 on the marker while the angle of entry and depth of penetration are additionally guided by the forward circular projection 32.

Another embodiment of the present invention is illustrated by FIG. 5 which is a perspective view of a hypodermic needle sheath 34, said needle sheath 34 featuring linear patterning projections 35 integral with its structure. In the embodiment shown in FIG. 5, one of the patterning projections 35 extends forward across the closed end-cap 36 of the needle sheath 34, and a projection 38 intersects the projection 35 perpendicularly. FIG. 5A is a top view of the mark made by this needle sheath embodiment wherein the operator preferably impresses the side patterning projections 35 first, and, by angling the open end of the needle sheath upwardly so that the long axis of the sheath becomes perpendicularly oriented to the skin, the cross-marked pattern 38 on the closed-end cap 36 is readily transferred to the skin by brief, compressive contact. The cross-mark serves primarily as a guide for the final entry of a needle (or other invasive device) into the selected vessel once the initial site of penetration and the needle's axial orientation are established by the longitudinal projections 35.

Patterning projections such as 35 in FIG. 5, and 24 and 26 in FIG. 2, can be affixed to, or incorporated in, protective wrappings and assemblies of all types as well as common medical and surgical devices such as probes, cannulas, syringes, infusion sets and associated paraphernalia for point-of-use availability. Similarly, the needle sheath 34, while serving its accustomed function of protecting an encased needle and assuring sterility, is also conveniently available as a marker for venipuncture or other invasive procedures at the operator's option.

Because needle sheaths are generally tubular, as will be known to those skilled in the art, the axially-oriented patterning projections 35, extending from the non-planar surfaces of the sheath, are of varying height so that, as preferred, their tapered edges terminate in and define a common horizontal plane. Thus, measuring perpendicularly from the needle sheath surface, the center projection will not project outwardly as much as the two projections on either side of it, as shown in FIG. 5., thereby defining a horizontal plane between them. Alternatively, when formed on a planar surface the projections 35 can be of equal height, as shown at 31 in FIG. 3A.

FIGS. 6 and 7 show alternate needle sheath embodiments. FIG. 6 is a perspective view of a needle sheath 40 having two linear projections 41 along the surface 42 of the sheath 40, and separate intersecting projections 44 on the closed end 46 of the needle sheath 40. When using this embodiment, the operator may conveniently choose a single pattern (i.e. either the cross-mark pattern 44, or the linear pattern 41) to the exclusion of the other. The cross-mark 44, for example, might be preferably employed to mark a particular site for intramuscular injection, tissue biopsy, or fluid aspiration. When employed cooperatively (especially for venipuncture), the projections 41 and 44 may be impressed into the skin in any order although the parallel projections 41 are generally the first employed. Thus while the parallel projections 41 provide directional guidance in delineating a selected artery or vein, the cross-mark projections 44 actually target the site for final vascular entry. FIG. 6A is a top view of a mark employing both patterns of FIG. 6.

FIG. 7 is a perspective view of a needle sheath 50 having parallel linear projections 52 affixed thereto, angularly projecting outwardly from the arcuate surface 54 of the sheath 50 and at right angles to the plane of the closed end 56 of the sheath. A set of projections 58 is also affixed at right angles to the plane of end 56 so as to visually direct the placement of the markers 52 directly over a selected vessel as well as to subsequently impress a dual mark highlighting an appropriate endpoint for final vascular entry (e.g., see FIG. 4). FIG. 7A is a top view of the mark obtained when all the patterning elements of the needle sheath 50 of FIG. 7 are cooperatively employed.

FIG. 8 is a perspective view of an alternate embodiment of a needle sheath 60 having linear projections 62 affixed thereto along the surface 64 and continuing along the closed end 65 of the needle sheath 60. Another, tapered, circular element 66 extends from the sheath's open and opposite end 68 so that either the open or closed ends of the sheath can be used to impress a distinctive mark. The larger, circular mark made by the tapered extension 66 at the open end may be preferred, for example, to delineate an area for biopsy or to outline a site for injection such as in the upper, outer, quadrant of the buttocks.

Additional patterns may readily be formed by the combined effects of the respective patterning elements. For example, the three linear projections 62 extending along the closed end 65 create a four-chambered grid when the marker is axially rotated 90 degrees and a second impression is then superimposed directly over the existing mark.

FIG. 9 shows still another embodiment of the invention wherein a needle sheath 70 has a single projection 72 extending along the surface 74 and partially along the closed end 75, to designate the location of a vein and to visually assist in directionally guiding placement of the marker over the selected vessel. A second projection 76 intersecting projection 72 at right angles thereto is also affixed along the surface 74 of the needle sheath 70 to provide a suitable reference point for entering the skin. FIG. 9A is a top view of the mark obtained using the needle sheath 70.

FIGS. 10 and 10B show another embodiment of the invention wherein a needle sheath 80 has a single projection 82 extending along its tubular surface 84. A central, tapered circular projection 86 is affixed to or formed on a recessed, closed end-cap 88 of the sheath 80. The forward projecting wall of the sheath is tapered and extends beyond the end-cap 88 to define a common plane with the smaller central projection 86 (i.e., they both extend the same distance, e.g., about 1.5 mm, beyond the surface plane defined by the end-cap).

FIG. 10A shows the impression made by the linear projection 82 in conjunction with the circular projections 86 and 89 of the marker provided by sheath 80. Alternatively, depending on the therapeutic or diagnostic procedure involved, either the linear or circular projections might be used alone.

Figure 11:
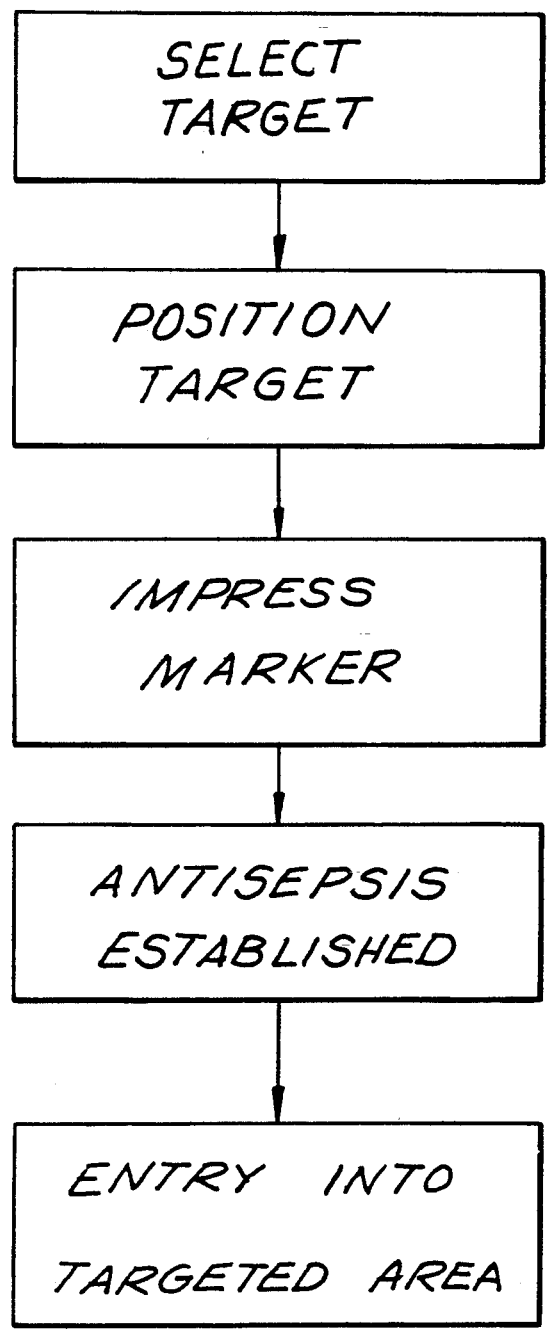
FIG. 11 is a block diagram illustrating the method of the invention.

The method of the invention is outlined in FIG. 11 which illustrates the steps of the method in block diagram form in accordance with the following operations:

a) A target is initially selected and evaluated;

b) A suitable marker is positioned on the skin, above or adjacent to the desired target, and aligned by inspection and palpation;

c) The patterning elements on the marker are impressed into the skin to produce the desired directional and positioning markings;

d) The location of the target relative to the directional and positional marks is visually and tactually confirmed;

e) An aseptic field is thereafter established; and f) The target is sterilely entered with the aid and guidance of the established marks.

Thus, according to the present process, first, the operator chooses an appropriate area for the intended procedure and a particular site is selected, usually by a combination of direct visual observation and palpation. In the case of intravenous insertion, for example, desirable veins in the hand or arm are distended by the application of a tourniquet proximal to the targeted site. When the target site has been defined to the operator's satisfaction, the marker is placed on the skin over or immediately adjacent to a selected point-of-entry. The optimum position and alignment of the marker are carefully confirmed by thorough inspection and palpation.

Once suitably positioned, the marker is manipulated and sufficient pressure is applied by the operator to bring the patterning projections of the marker into firm, compressive contact with the skin, usually for 2-5 seconds. When the marker is removed, a series of temporary markings remain on the skin, as shown in the various Figures hereinabove, having been impressed into the underlying skin by the patterning projections. Depending on the skin thickness, the duration of contact and the degree of pressure applied, a distinctive pattern can be expected to remain clearly visible for several minutes. At this time the target is visually and palpably aligned with elements of the mark, thereby providing clear directional guidelines and distinctive positioning cues to the operator.

After the skin is marked, the area around and over the mark is rendered antiseptically clean by thorough washing with soap, alcohol, iodine and/or other antimicrobial agents.

With aseptic safeguards and orienting marks securely in place, further non-sterile contact with the targeted area is neither desirable nor necessary. The target site can be easily located and a selected point-of-entry accurately identified by visual reference to the guiding marks. Insofar as further manipulation and additional palpation are no longer required, the skin may be safely and accurately penetrated while maintaining aseptic conditions and preserving the integrity of the antiseptic field.

The method of the invention also reduces the manner and number of incorrect placements, thereby significantly reducing discomfort and danger to the patient. This includes, but is not limited to, aborted procedures, excessive bleeding, wound infection, sepsis, protracted pain and extraneous injury to neighboring tissues and organs.

As previously indicated, the marking technique of the present invention may be utilized to facilitate the insertion of any medical or surgical instrument through the skin, e.g., biopsy punches, trochars, scalpel blades, probes and the like, as well as hypodermic needles and cannulas. Since these and other changes may be made in the preferred embodiments described herein, the scope of the invention should be construed in accordance with the claims appended hereto.

I claim:

1. An independently hand-held device for marking the surface of the skin to identify a selected area for a diagnostic or therapeutic procedure, which comprises
   (a) a supporting body;
   (b) one or more firm patterning elements extending in relief from the supporting body for impressing directional and/or positioning markings on the skin through brief compressive contact; and
   (c) a marking element extending in relief from the supporting body for impressing a positioning marking on the skin for identifying a target site for a medical or surgical instrument.

2. A device according to claim 1, wherein the patterning elements are thin-edged, tapered projections on the supporting body.

3. A device according to claim 1, wherein one or more of the patterning elements is a thin-edged tapered projection of the supporting body.

4. A device according to claim 1, wherein two or more patterning elements share a common plane of origin on the supporting body.

5. A device according to claim 1, wherein at least one of the patterning elements projects outwardly at substantially right angles to a planar surface of the supporting body.

6. A device according to claim 1, wherein the skin-impressing edges of at least one group of patterning elements projecting from a given surface of the supporting body terminate on a single plane substantially perpendicular to said elements.

7. A device according to claim 1, wherein the patterning elements project outwardly from a non-planar surface on the supporting body and are thin-edged tapered projections which terminate on a single plane substantially perpendicular to said elements.

8. A device according to claim 1, wherein the patterning elements project outwardly at least 0.2 millimeter from their respective origins on the supporting body.

9. A device according to claim 1, wherein one or more of the patterning elements is substantially linear.

10. A device according to claim 1, wherein two or more of the patterning elements are substantially parallel to one another.

11. A device according to claim 1, wherein one or more of the patterning elements is substantially curved.

12. A needle sheath or cover for marking the skin to identify a selected target site for the insertion of a needle or other invasive device, which comprises:
   (a) a tubular body,
   (b) one or more firm patterning elements extending in relief from the tubular body for impressing directional markings on the skin through brief compressive contact, and
   (c) a marking element formed on the tubular body for impressing a positional marking on the skin related to said directional markings and for identifying said target site.

13. The needle sheath or cover of claim 12, wherein one or more of the patterning elements is substantially parallel to the longitudinal axis of the supporting body.

14. The needle sheath or cover of claim 12, wherein the marking element is defined by the intersection of two or more of the patterning elements.

15. The needle sheath or cover of claim 12, wherein the marking element is defined by at least one circular projection formed on one end of the needle sheath of cover.

16. A method for locally and directionally marking an anatomical site on a patient's skin for a diagnostic or therapeutic procedure, which comprises:
    (a) selecting a targeted anatomical site;
    (b) positioning a hand-held marking device on the skin on or adjacent to the targeted site, said device comprising a supporting body having one or more firm patterning elements extending in relief from the supporting body for impressing directional markings on the skin:
    (c) impressing the patterning elements into the skin to form the desired directional markings thereon;
    (d) removing the marking device from the skin;
    (e) rendering the skin antiseptically clean; and
    (f) utilizing the directional markings on the skin as guides for sterilely accessing the targeted site.

17. The method of claim 16,
    wherein the marking device further includes a marking element extending in relief from the supporting body for impressing a positioning marking on the skin to identify the targeted site; and
    wherein the marking element is impressed into the skin in step (c) to form the desired positioning marking thereon, and the positioning marking is also utilized in step (f) as a guide for sterilely accessing the targeted site.

18. The method of claim 16,
    wherein the marking device comprises a needle sheath or cover having a tubular supporting body with one or more firm patterning elements extending in relief from the tubular body, and
    wherein the directional markings are utilized in step (f) as guides for inserting a needle or other invasive device through the skin to impinge on said targeted site.

19. The method of claim 18,
    wherein the marking device further includes a marking element extending in relief from the tubular body for impressing a positioning marking on the skin to identify the targeted site; and
    wherein the marking element is impressed into the skin in step (c) to form the desired positioning marking thereon, and the positioning marking is also utilized in step (f) as a guide for inserting the needle or other invasive device through the skin to impringe on said targeted site.

20. A method for marking an anatomical site on a patient's skin for a diagnostic or therapeutic procedure, which comprises:
    (a) selecting a targeted anatomical site;
    (b) positioning a hand-held marking device on the skin on or adjacent to the targeted site, said device comprising a supporting body having one or more firm elements extending in relief from the supporting body for impressing directional or positioning markings on the skin;
    (c) impressing said elements into the skin to form the desired markings thereon;
    (d) removing the marking device from the skin;
    (e) rendering the skin antiseptically clean; and
    (f) utilizing the marking on the skin as guides for sterilely accessing the targeted site.

* * * * *